(12) United States Patent
Petraglia et al.

(10) Patent No.: US 8,012,091 B2
(45) Date of Patent: Sep. 6, 2011

(54) METHOD AND SYSTEM FOR FETAL WEIGHT ESTIMATION

(75) Inventors: Felice Petraglia, Siena (IT); Paolo Barbini, Siena (IT); Gabriele Cevenini, Siena (IT); Filiberto Maria Severi, Castelnuovo Berardenga (IT)

(73) Assignee: Esoate S.p.A., Milan (IT)

( * ) Notice: Subject to any disclaimer, the term of this patent is extended or adjusted under 35 U.S.C. 154(b) by 1150 days.

(21) Appl. No.: 11/484,099

(22) Filed: Jul. 11, 2006

(65) Prior Publication Data

US 2007/0038093 A1   Feb. 15, 2007

(30) Foreign Application Priority Data

Jul. 11, 2005   (EP) .................................... 05425498

(51) Int. Cl.
*A61B 8/00* (2006.01)
(52) U.S. Cl. .......... 600/437; 600/408; 600/438; 700/47; 700/48
(58) Field of Classification Search .................. 600/437, 600/438, 449, 408; 700/47–48
See application file for complete search history.

(56) References Cited

U.S. PATENT DOCUMENTS

| | | | | |
|---|---|---|---|---|
| 6,004,267 A | * | 12/1999 | Tewari et al. | 600/300 |
| 6,575,907 B1 | | 6/2003 | Soferman et al. | 600/438 |
| 6,695,780 B1 | | 2/2004 | Nahum et al. | 600/437 |
| 2004/0122882 A1 | * | 6/2004 | Zakharov et al. | 708/446 |

FOREIGN PATENT DOCUMENTS

EP   1473667 A2   11/2004

OTHER PUBLICATIONS

Zhang et al., "Neural Network Based Systems for Prostate Cancer Stage Prediction", IEEE, 2000, pp. 659-662.*
Chuang, L. et al., "Ultrasound Estimation of Fetal Weight with the Use of Computerized Artificial Neural Network Model", *Ultrasound in Medicine and Biology*, New York, NY, vol. 28, No. 8, Aug. 2002, pp. 991-996.
Specht, D.F., "Probabilitist Neural Networks", *Neural Networks*, Elsevier Science Publishers, Barking, GB, vol. 3, No. 1, Jan. 1990, pp. 109-118.
Farmer, R. M. et al., "The Use of a Neural Network for the Ultrasonographic Estimation of Fetal Weight in the Macrosomic Fetus", *American Journal of Obstetrics and Gynecology*, vol. 166, No. 5, May 1992, pp. 1467-1472.
Mol et al., "Implementation of Probabilistic Decision Rules Improves the Predictive Values of Algorithms in the Diagnostic Management of Ectopic Pregnancy", *Human Reproduction*, vol. 14, No. 11, 1999, pp. 2855-2862.

(Continued)

*Primary Examiner* — Ruth S Smith
*Assistant Examiner* — Christopher Cook
(74) *Attorney, Agent, or Firm* — Woodard Emhardt Moriarty McNett & Henry LLP

(57) ABSTRACT

A method for fetal weight estimation wherein fetal biometric parameters are ultrasonically measured and further physiological and phenomenological pregnancy parameters are determined for a plurality of sample cases. The fetal weight for each of the sample cases is then determined by precision weighing at birth. A database is then created based on the known sample cases and mathematical prediction models are generated from the database. For the case under examination for which fetal weight is to be predicted, the fetal biometric parameters are ultrasonically measured and further physiological and phenomenological pregnancy parameters are determined. The fetal weight of the case under examination is predicted by using a mathematical prediction model and a multinormal probabilistic model is used as a mathematical model.

31 Claims, 5 Drawing Sheets

OTHER PUBLICATIONS

Perronnin et al., "A Probabilitist Model for Face Transformation with Application to Person Identification", *Eurasip Journal on Applied Signal Processing,* vol. 2004, No. 4, Apr. 2004, pp. 510-521.

Folland et al., "Comparison of Neural Network Predictors in the Classification of Tracheal-Bronchial Breath Sounds by Respiratory Auscultation", *Artificial Intelligence in Medicine,* vol. 31, No. 3, Jul. 2004, pp. 211-220.

* cited by examiner

METHOD AND SYSTEM FOR FETAL WEIGHT ESTIMATION

CROSS-REFERENCES TO RELATED APPLICATIONS

The present application claims the priority benefit of European Patent Application Ser. No. 05425498.2, filed Jul. 11, 2005, which is hereby incorporated by reference in its entirety.

BACKGROUND OF THE INVENTION

The invention relates to a method for estimating fetal weight which comprises the following steps:

a) Ultrasonically measuring fetal biometric parameters, particularly fetal head, abdominal and limb dimensions of sample cases;

b) Determining further physiological and phenomenological pregnancy parameters of these sample cases;

c) Determining the fetal weight of the sample cases by precision weighing at birth;

d) Creating a database of these known sample cases, in which each record associated to each known case comprises the fetal biometric parameters, the additional physiological and phenomenological pregnancy parameters and the fetal weight as determined at birth;

d) Generating mathematical prediction models from the database of known cases;

e) Ultrasonically measuring said fetal biometric parameters, particularly fetal head, abdominal and limb dimensions of the cases under examination, for which fetal weight is to be predicted;

f) Determining further physiological and phenomenological pregnancy parameters of these cases under examination, for which fetal weight is to be predicted;

g) Predicting the fetal weight of said cases under examination by using the mathematical prediction models generated in step d.

Obstetric management of deliveries is affected by gestational age and fetal weight. At present, an accurate ultrasonographic examination, as well as the comparison of certain ultrasound biometric parameters of the fetus with respective normal curves, particularly before the 20th week of pregnancy, provides reliable gestation dating. However, many problems are still associated to fetal weight estimation by ultrasonic measurement of standard biometric parameters, usually relating to geometric head, abdominal and limb dimensions. In modern perinatology, fetal growth monitoring is of the utmost importance, for its being strictly related to fetus health. The detection of alterations in fetal growth allows to optimize pregnancy management.

Intensive research has been conducted for the last 30 years and led to the publication of many fetal weight estimation models from intrauterine ultrasound in specialized reviews. Most of these models are based on empirical mathematical formulas, determined from statistical regression methods, and only a few of them are based on physical principles; in recent times, a few models based on Artificial Neural Networks (ANN) have been documented.

Clinical use of these models has produced an increased number of ultrasound examinations which also specify fetal weight. Although these models are effective in original experiments, ordinary practical experience shows that the various formulas that have been proposed in the literature prove a considerably lower reliability in their clinical use.

The difference between the accuracy documented in the literature and that obtained in practical cases is likely to be caused by measurement procedures, model generation methods and sampling errors. More specifically, in most cases, statistical linear and non linear regression models are used, whose mathematical formulas contain parameters to be estimated by minimizing the quadratic error. The latter is evaluated by using ultrasound data acquired not more than six days before birth, which data may be associated to the real fetal weight, considered equal to the newborn weight, measured with precision scales. Estimates of model parameters are often based on a small number of data items relating to cases that do not wholly represent the entire population, and sometimes fetuses in a too homogeneous weight range are used.

Attempts to reduce the absolute error, by introducing correction factors in the algorithm, as well as new information such as the amount of amniotic fluid, the number of fetuses and any maternal pathologies, and new ultrasound biometric parameters differing from routinely measured parameters have produced no significant improvement. The new mathematical formulas still have the above drawbacks, and further require the use of unusual ultrasound biometric parameters, which often involve higher measurement difficulties, especially for operators having little experience.

In short, regardless of the method in use, in clinical practice human and instrumental measurement errors affect the accuracy of fetal weight estimation, and the average absolute error with respect to the real weight is never below 7-8%. While this value would be acceptable in itself, a high standard deviation causes more than a quarter of cases to be estimated with an error of more than 10% which value is often considered a threshold above which the estimation is deemed not to comply with a proper clinical use.

This makes the method unsuitable for effective assistance in clinical decision, especially due to increasingly frequent legal implications of a wrong medical decision. Furthermore, the error tends to increase when the estimation is aimed at diagnosing fetal macrosomia. It was found that, in case of abnormal fetal growth, the absolute error on fetal weight for the various models is often of more than 10-15%. Moreover, the precision of mathematical formulas of weight prediction decreases when weight estimation should be more accurate. In all proposed models, a generalized tendency is observed toward over/underestimation of weight of macro/microsomic fetuses. None of the proposed models can provide significantly better estimates than the other models. In practice, there exist about ten formulas which provide the best results with no significant differences therebetween.

Since most clinical problems relate to microsomic fetuses (below 2500 g) and to macrosomic fetuses (above 4000 g), mention should be also made to many specific models that have been developed in the literature with the purpose of providing more accurate estimates in these weight ranges. Although some of these specific models provide significantly lower errors for microsomic and macrosomic fetuses, they have the serious drawback of being only accurate for previously diagnosed microsomic or macrosomic fetuses. Such an a priori classification is not easy at all, especially for borderline cases, which are the most important cases from the clinical point of view. An error in this a priori classification involves the use of a totally unsuitable specific model, with a dramatic increase of the estimation error. This implies increased health care risks and heavier legal implications for operators.

More complex attempts to create models on partly overlapping weight ranges to obviate or at least attenuate the problem of a priori classification errors do not introduce actual improvements with respect to the use of a single model for all fetuses.

The conclusion is that the use of models for specific weight ranges is not convenient.

Therefore, the reliability of fetal weight estimates from ultrasound biometric measurements and pregnancy-related information is hitherto highly questionable, particularly for fetuses whose neonatal weight is situated on either side of normal distribution, i.e. the above mentioned microsomic and macrosomic fetuses.

However, since the accuracy of estimates is actually close to the threshold for useful use thereof in clinical decision, it is highly desirable to find effective solutions to reduce the error just as little as is sufficient to assure effectiveness of the method.

At present, birth weight prediction accuracy seems to be only improvable by basically trying to reduce the human error associated to the use of the ultrasound imaging apparatus to measure the main fetal dimensions in utero. Operators with a longer experience in the field of fetal ultrasound are known to provide a significantly lower error level than less expert operators, although the former still have unacceptable inaccuracy margins on particularly difficult cases.

This invention is based on the problem of improving a method of the type described hereinbefore so that the problems of the above prior art methods may be obviated without requiring heavier loads of computation and/or detection of ultrasound biometric and/or physiological and phenomenological pregnancy parameters.

Particularly, besides providing a more accurate fetal weight estimate, the invention has the object of providing probabilistic data on the reliability or consistency of the measurements of ultrasound biometric parameters and/or physiological and/or phenomenological pregnancy parameters with the actually obtained fetal weight estimate, to allow real-time corrections based on new measurements of such parameters.

The invention has the further object of providing a method as described hereinbefore, which may be easily managed by the operator and allow direct and immediate data reading.

Therefore, the invention proposes a method as described hereinbefore, in which fetal weight is predicted on the basis of sample case data, relating to ultrasound biometric parameters and/or physiological and/or phenomenological pregnancy parameters, by using a mathematical multivariate Gaussian probabilistic model.

The use of a probabilistic model provides a number of advantages: the main advantage, in the specific case of this invention, is to provide unbiased estimates, i.e. with no systematic over/underestimates of micro/macrosomic fetuses. Furthermore, the mathematical multivariate or multinormal model allows to associate probability levels to estimates, to evaluate both the reliability of the estimated weight, and the mutual consistency of the measurements of ultrasound biometric parameters and/or physiological and/or phenomenological pregnancy parameters.

The invention further relates to a system for determining the fetal weight, characterized in that it comprises a computer having at least one data input device and at least one display monitor and in which a computer program is or may be loaded, wherein the algorithms of the multinormal model, the interfaces for access to sample case database data, and the algorithms of the mean vector and covariance matrix estimation model, as well as the code for displaying the neonatal weight estimate and the probability thereof are coded.

Further characteristics and improvements will form the subject of the dependent claims.

The characteristics of the invention and the advantages derived therefrom will appear more clearly from the following description of a few embodiments, with reference to the annexed drawings.

BRIEF SUMMARY OF THE INVENTION

A method for fetal weight estimation, comprising the following steps: (a) Ultrasonically measuring fetal biometric parameters; (b) Determining further physiological and phenomenological pregnancy parameters; (c) Determining the fetal weight by precision weighing at birth; (d) Creating a database of known sample cases; (e) Generating mathematical prediction models from the database of known cases; (f) Ultrasonically measuring the fetal biometric parameters; (g) Determining further physiological and phenomenological pregnancy parameters; and (h) Predicting the fetal weight of the cases under examination by using a mathematical prediction model, characterized in that a multinormal probabilistic model is used as a mathematical model.

One object of the present invention is to provide an improved method for estimating fetal weight.

Related objects and advantages of the present invention will be apparent from the following description.

DETAILED DESCRIPTION OF THE INVENTION

Figure 1:
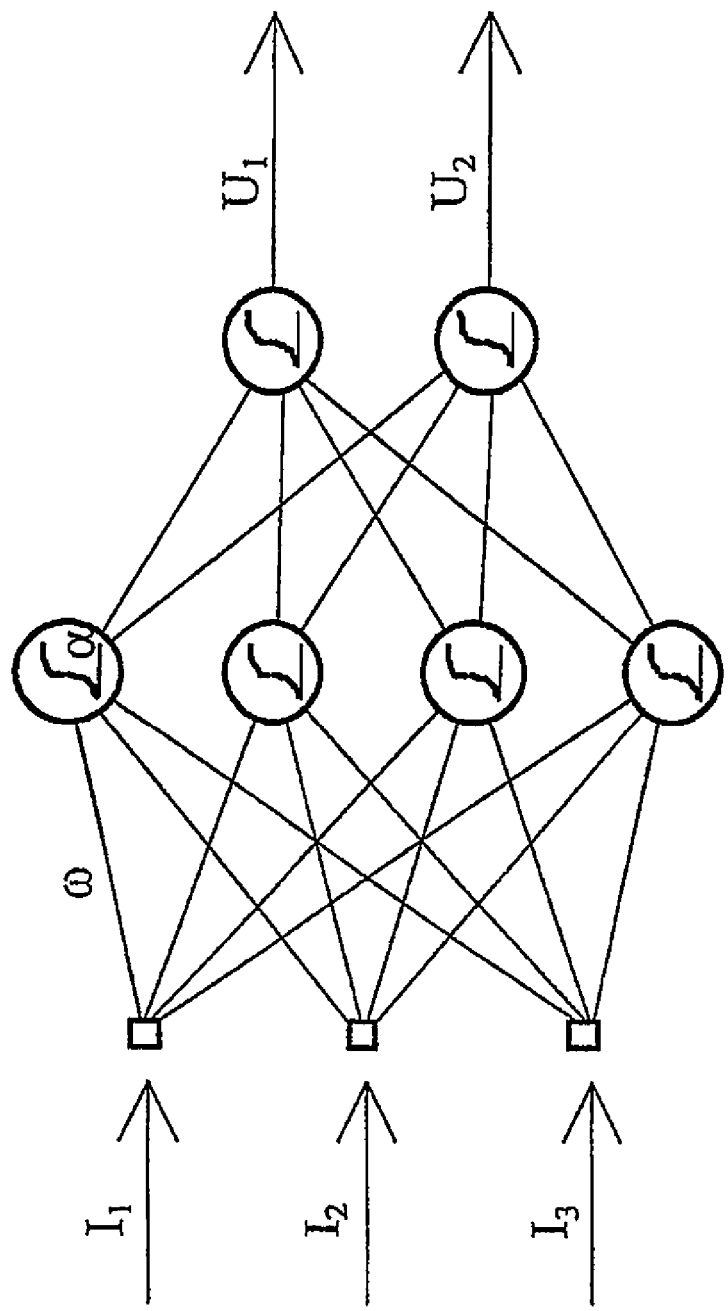
FIG. 1 shows a feed-forward neural network having three inputs (I1, I2, I3) and 2 outputs (U1, U2).

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Theory of the Multinormal Probabilistic Model

During fetal ultrasound in the last week of pregnancy of about 4000 women, measurements of the Head circumference (HC), Abdominal Circumference (AC), Biparietal Diameter (BPD) and Femur Length (FL). Ultrasound was performed by expert operators in 15 centers all over the country. The gestational age was related to the first day of the last menstrual period (MA) and was determined by an accurate reconstruction of menstrual history, confirmed by an ultrasonographic examination dating before the 20th week of gestation.

Fetal weight was estimated by using a procedure based on a multinormal probabilistic model and Artificial Neural Networks (ANN). The probabilistic model is a five-dimensional model and expresses the probability of all 4 ultrasound biometric measurements as well as the gestational age, associated to each weight at birth (WB) and other important pregnancy information, specifically the amount of amniotic fluid (AF), the number of fetuses (NF) and the number of days to delivery (DD).

- WB is a quantitative variable, which is typically measured with a resolution of 10 grams, and in a range of 400 to 6000 grams;
- AF is a quantitative variable, having 4 possible categories: normal, none, decreased or increased amniotic fluid; it can be turned into quantitative values by 2-bit binary coding;
- NF is a discrete quantitative variable and is expressed as 1, 2 or 3 (more than 2 fetuses);
- DD is a discrete quantitative variable and ranges from 0 (delivery on the same day as the ultrasound examination) to 6 days (ultrasound performed one week before delivery).

Thus, the model may be expressed in terms of the following probability density of observations x, as influenced by data w:

$$p(x/w) = \frac{1}{(2\pi)^{d/2}|\Sigma(w)|^{1/2}} \exp\left\{-\frac{1}{2}[x-\mu(w)]^T \sum_w^{-1}[x-\mu(w)]\right\} \quad (1)$$

x is the vector of the 5 parameters (variables xi, i=1, 2, . . . , 5), i.e. the ultrasound biometric parameters and the phenomelological pregnancy parameter, that is $$x = [x1\ x2\ x3\ x4\ x5] = [MPD\ HC\ AC\ FL\ MA]; \quad (2)$$

w is the vector that contains the weight at birth (WB) and the other data (variables wj, j=1, 2, . . . , 4), that is $$w = [w1\ w2\ w3\ w4]32\ [WB\ AF\ NF\ DD]; \quad (3)$$

d is the dimension of the multidimensional space of these parameters, in this case d=5;

$\mu(w)$ and $\Sigma(w)$ are the mean vector and the covariance matrix of the parameters, which are functions of data w and in which $$\mu(w) = [\mu1(w)\mu2(w)\mu3(w)\mu4(w)\mu5(w)] = [BPDm(w)HCm(w)ACm(w)FLm(w)MAm(w)] \quad (4)$$

where the subscript m in ultrasound biometric parameters denotes their mean value $$\Sigma(w) = \begin{bmatrix} \sigma_{x_1}^2(w) & \sigma_{x_1 x_2}(w) & \sigma_{x_1 x_3}(w) & \sigma_{x_1 x_4}(w) & \sigma_{x_1 x_5}(w) \\ \sigma_{x_2 x_1}(w) & \sigma_{x_2}^2(w) & \sigma_{x_2 x_3}(w) & \sigma_{x_2 x_4}(w) & \sigma_{x_2 x_5}(w) \\ \sigma_{x_3 x_1}(w) & \sigma_{x_3 x_2}(w) & \sigma_{x_3}^2(w) & \sigma_{x_3 x_4}(w) & \sigma_{x_3 x_5}(w) \\ \sigma_{x_4 x_1}(w) & \sigma_{x_4 x_2}(w) & \sigma_{x_4 x_3}(w) & \sigma_{x_4}^2(w) & \sigma_{x_4 x_5}(w) \\ \sigma_{x_5 x_1}(w) & \sigma_{x_5 x_2}(w) & \sigma_{x_5 x_3}(w) & \sigma_{x_5 x_4}(w) & \sigma_{x_5}^2(w) \end{bmatrix} \quad (5)$$

The covariance matrix (5) is symmetric with respect to the principal diagonal, that is $$\sigma_{x_i x_j} = \sigma_{x_j x_i} \quad (6)$$

It represents a measure of variability for multidimensional quantities: in the principal diagonal it contains the variances of each variable xi, i.e. the mean-square deviation of data from their mean value, whereas in the other positions it contains the covariance of each pair of variables, i.e. the mean of the product of deviations from the respective mean value. The covariance of two variables is known to describe their degree of association: when it is zero, there is no relation between the two variables, and when it has high values, there is a high degree of relation, which is a direct relation for positive values and an inverse relation for negative values.

The model (1) is entirely defined by its parameters $\mu(w)$ and $\Sigma(w)$. These are 5 mean values, 5 variances and 10 covariances. However, these parameters are dependent on w, therefore estimation thereof from sample data with ordinary methods is scarcely ever possible in a direct manner and often provides inaccurate estimates, and thence unreliable results. Theoretically, if the available sample data were in a sufficient number, these parameters might be estimated from such data by simply using the mathematical definition of the parameters being examined.

In other words, if a sufficient number of data were available for each of the possible finite combinations of vector w, the elements of the mean vector and the covariance matrix might be estimated as follows:

$$\bar{\mu}_i(w) = \frac{\sum_{k=1}^{N} x_{i_k}(w)}{N} \quad (7)$$

$$\bar{\sigma}_{x_i}^2(w) = \frac{\sum_{k=1}^{N} [x_{i_k}(w) - \bar{\mu}_i(w)]^2}{N-1} \quad (8)$$

$$\bar{\sigma}_{x_i x_j}(w) = \frac{\sum_{k=1}^{N} [x_{i_k}(w) - \bar{\mu}_i(w)][x_{j_k}(w) - \bar{\mu}_j(w)]}{N-1} \quad (9)$$

where the overscored symbols denote the estimates of their respective parameters and summations are extended to all N data of the variable xi which have the same combination of values as the data vector w. This has to be repeated for any combination of w.

The elements of vector w, as defined herein, provide a great number of possible combinations (regions of space w), wherefor data is insufficient for estimates to be accurate; in certain regions of the space w, data is even absent. This problem may be obviated either by reducing the number of combinations of w, thereby causing a loss of important information, and without ultimately solving the problem, or by applying a simple mathematical w-dependency rule, itself parametrizable, to the parameters to be estimated. In this case, the problem would be shifted to the estimation of the parameters of these mathematical relations, using all available data and appropriate regression methods. While this approach is feasible, it has a number of drawbacks, the most serious whereof is the need of preventively setting w data dependency rules, which are not known per se because they partly represent the relevant object of this model, i.e. fetal weight.

Artificial Neural Networks for Estimation of the Mean Vector and the Covariance Matrix of the Multinormal Model In accordance with this invention, the problem of estimating the mean vector and the covariance matrix of the multinormal fetal or neonatal weight determination model is solved by the combined use of multiple Artificial Neural Networks (ANN), which excellently solve the problem.

These ANNs have been developed in cognitive sciences and bioengineering. Their structure is derived from the nervous system of living beings. They have the peculiarity of possessing many processing units (neurons), arranged in different layers and joined together by particular connections (synapses). Among the various classes of ANNs, feed-forward networks may be found. In these networks, information only flows in the forward direction from inputs to outputs (see FIG. 1).

FIG. 1 is a schematic representation of a feed-forward neural network having 3 inputs (I1, I2, I3), 2 outputs (U1, U2), a hidden layer with 4 neuron units and an output layer with 2 neuron units. The inputs are linearly combined by synaptic weights $\omega$. Each neuron is activated by afferent synapses, based on a threshold $\alpha$ and on an activation function. Neuron activation propagates forwards always in the same manner.

There already exist many applications of ANNs in a number of medical fields, to assist clinical decisions, and they often improve to a significant extend diagnostic accuracy. Effective advantages as compared with traditional mathematical and statistical regression models are achieved thanks to the following characteristics:

there is no need for prior design of a special mathematical model and/or for making a priori hypotheses about the structure of the model;

input data may be added, without redesigning the mathematical structure of the model;

if the ANNs are designed with a sufficient number of neuron units and synapses, they allow to approximate uniformly (in a continuous domain) and in the best possible manner, the relations between the input predictive variables and the outputs (predicted variables), even though such relations may be complex and non linear;

they may be trained with examples (real data) with the help of numerical algorithms, to make the knowledge so acquired available for decisional purposes;

the relations existing among the input variables are naturally described by the distributed representation and the mathematical ANN representing expressions; this allows a sort of intrinsic reduction of dimensionality, which is known to be highly advantageous in terms of generalization, i.e. the ability of maintaining the predictive performances acquired on training data unchanged on new data and situations.

the training process may be effectively controlled to prevent the so-called overfitting, which occurs in many unnecessarily complex models, and leads to poor generalization; in other words, overfitting is the ability to store training data without being able to generalize it to new situations.

An ANN is trained by introducing known input and output data and by estimating, with the help of numerical optimization algorithms, the weights of synaptic connections and the values of neuron activating thresholds, which provide a better representation of input-output relations.

Nevertheless, for the present problem of estimating the mean vector and the covariance matrix of the multinormal model to determine the fetal or neonatal weight, the application of an ANN is neither a simple direct use of the neural network according to prior art teachings, nor a simple training and configuration step.

Neural networks are complex algorithms which often have convergence problems as well as long processing times and heavy computation hardware requirements. The present method should allow execution by unskilled personnel, having no specific expertise and on easily available and relatively low-cost commercial hardware. To this end, the invention suggests a solution in which a combination of three neural networks is used and preferably such neural networks, or the tasks thereof, are defined so that at least one of the neural networks is used to generate output data that can be stored in as a data table or a database, based on the sample data database. Particularly this is performed in a separate and independent step and, as further explained in the following description, the system for carrying out the method only has one software-integrated neural network and the above output data database of the other neural networks. This arrangement allows to restrict the intervention of expert personnel to the most difficult neural network operation step, which is an independent process step, and does not add any load to the computation of the fetal or neonatal weight by the final user.

Figure 2:
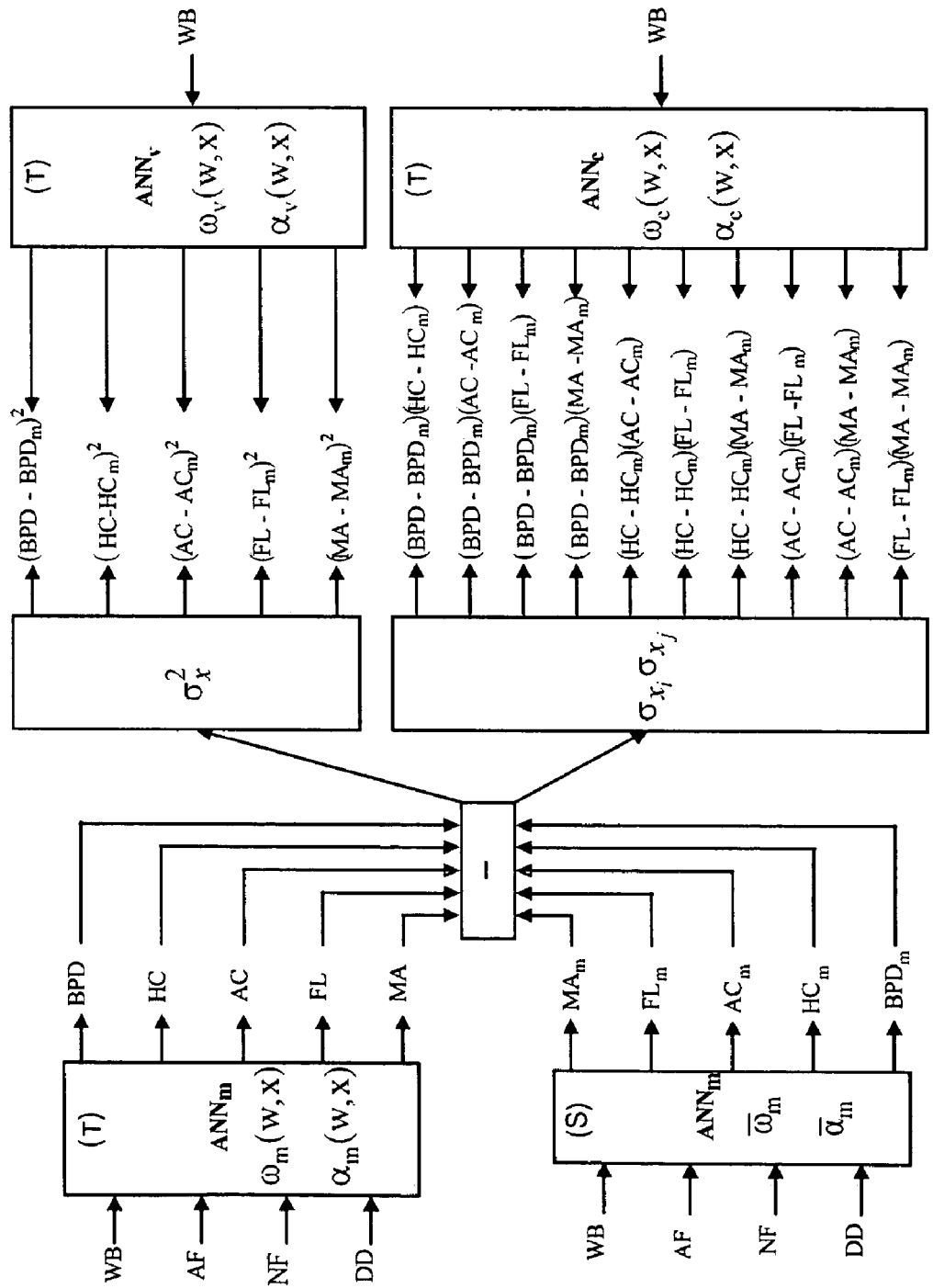
FIG. 2 shows a block diagram of the artificial neural networks that are used to estimate the mean vector and the covariance matrix of the multinormal probabilistic model expressed in equation (1).

According to this invention, the parameters of the multinormal model were estimated by using a combination of three ANNs was used, the first (ANNm) for estimating the mean vector, the second (ANNv) for estimating the variances of the covariance matrix (diagonal elements) and the third (ANNc) for the covariances of the same matrix (see FIG. 2). The three ANNs are all constructed with 2 neuron layers, having 10 neurons in the hidden layers with a logsig type activation function having a suitable threshold, whereas the output neurons have a linear activation function. The weights of synaptic connections and the neuron thresholds have been estimated in an iterative manner, by using a numerical descending gradient algorithm with adaptive moment and training speed. Overfitting is usually controlled by using the so-called early-stopping method, which consists in stopping the iterative training procedure performed on half of the data being trained (learning set) when the predictive error in the other data half (testing set) ceases to decrease, starts to increase again or decreases significantly less than in the learning set While early-stopping is an effective method, a different method was chosen, known as Bayesan filtering method (see handbook of Matlab 'Neural Networks' toolbox), because it assures a good generalization power, using all available training data, and provides improved smoothing properties, which are useful due to the discrete nature of data.

The properties of the above mentioned ANNs allow to effectively estimate the parameters of the probabilistic model (1) as well as their dependency on the data vector w. This is obtained by simply training the ANNs with the available data according to the scheme of FIG. 2, where the rectangular blocks represent the ANNs with 10 neurons in the hidden layer, that are used in the training (T) and simulation (S) steps.

Particularly, FIG. 2 shows a block diagram of the artificial neural networks that are used to estimate the mean vector and the covariance matrix of the multinormal probabilistic model expressed in equation (1).

The block diagram of FIG. 2 shall be interpreted as follows:

The ANNm is first trained with the available data (FIG. 2, top left) by presenting thereto the input data (vector w) and the corresponding output data (observation vector x) to estimate the synaptic weights ω (w,x) and the activation thresholds α (w,x), which depend on the components of the observation vector, i.e. on the biometric parameters of the fetus and on the one or more physiological and phenomenological pregnancy parameters. Particularly, as mentioned above, the selected parameters are standard parameters and the components of the observation vector x consist of ultrasound biometric data, which were measured during fetal ultrasound imaging: Head Circumference (HC) and Abdominal Circumference (AC), Biparietal Diameter (BPD) and Femur Length (FL), as well as physiological or phenomenological pregnancy parameters, and particularly: the gestational age, which was related to the first day of the last menstrual period (MA) and was determined by an accurate reconstruction of menstrual history, confirmed by an ultrasonographic examination dating before the 20th week of gestation.

Further physiological or phenomenological pregnancy parameters that may be measured before birth, although they are part of the data vector w, are: the amount the Amniotic Fluid (AF), the Number of Fetuses (NF), and the number of days to delivery (DD).

The estimates of synaptic weights $\bar{\omega}_m$ and neuron excitation thresholds $\bar{\alpha}_m$ so obtained allow such identified ANNm to simulate (FIG. 3, bottom left) the most reliable outputs for any combination of values WB, AF, NF and DD, even those that never occurred in the available data. These outputs may be reasonably considered as estimates of the mean vector μ(w) of the multinormal model (1). Particularly, by presenting to the input of the network the data that were used to train the ANNm, the output will give the corresponding estimated mean values of the ultrasound biometric measurements, as well as the gestational age.

Then, the deviations from the respective measurement means are determined (see block with minus sign). These deviations are squared (FIG. 2, top center), to be placed at the output of the ANNv during the training step (FIG. 2, top right), or suitably multiplied (FIG. 2, bottom center) to be placed at the output of the ANNc being trained (FIG. 2, bottom right).

Like for the ANNm, training of the ANNv and ANNc allows estimation of their respective synaptic weights and neuron excitation thresholds, which further provide the estimates of variances and covariances of the covariance matrix (5). As shown in FIG. 2, for estimation of variances and covariances, the inputs were reduced to the WB component only, assuming that the other data of vector w did not affect the variability of the phenomenon. In other words, the covariance matrix was deemed to only depend on the weight at birth WB. This simplification, which is appropriate and convenient to improve the efficiency of the fetal weight estimation software (see next paragraph) is not contradicted by the preliminary analyses and statistical tests for evaluating variance homogeneity in the various groups of AF, NF and DD.

Neural networks allow a uniform and continuous mapping of the input→output relation and identify the expected output values even when there is a small number of available data items, or there is no data at all. Therefore they represent herein an excellent method to estimate the parameters of the probabilistic model (1) from available data.

Interactive Software for Fetal Weight Estimation

In clinical practice, the problem arises of estimating fetal weight from pregnancy data and ultrasound biometric measurements. Particularly, given the values of AF, NF, DD, BPD, HC, AC, FL and GA (gestational age) for a pregnant woman, the value of FW is to be estimated. In other words, an estimate has to be produced of the first component WB of the data vector w, which obviously coincides with FW at the time of delivery, after determining the measured observation vector x and the data w relating to the amount of Amniotic Fluid (AF), the Number of Fetuses (NF), and the number of Days to Delivery (DD), except the quantity to be estimated, i.e. the fetal or neonatal weight.

The multinormal model of the expression (1) allows to trace probability curves (sometimes called percentiles) for each component of the data vector x, i.e. for the measured ultrasound biometric parameters, which in this example are Head Circumference (HC), Abdominal Circumference (AC), Biparietal Diameter (BPD), and Femur Length (FL), as well as gestational age.

Figure 3:
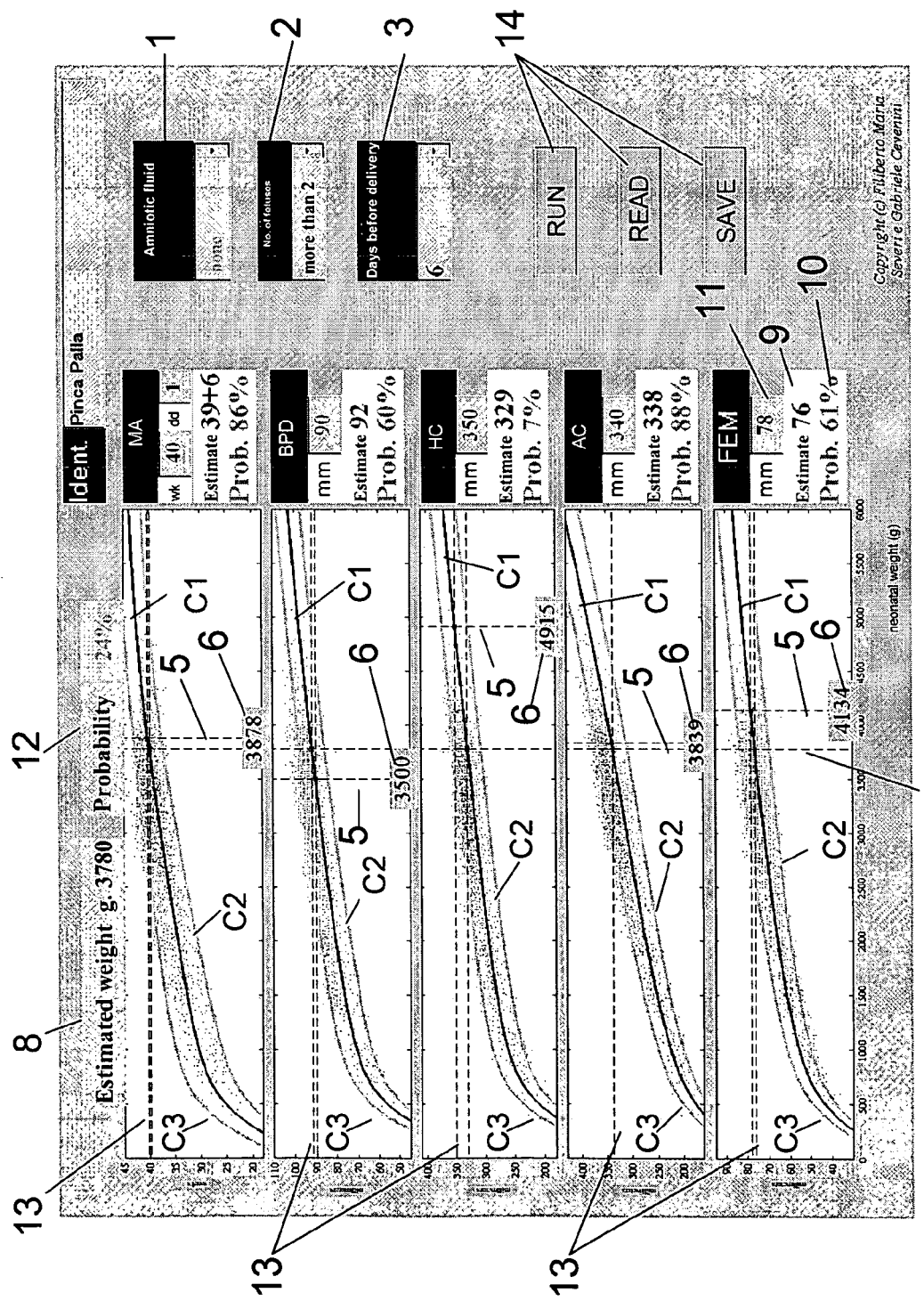
FIG. 3 shows a preferred embodiment of a graphic interface for fetal (or neonatal) weight estimation from ultrasound measurements and interactive control of measurement errors, and in which alphanumeric and graphic display is provided of fetal weight prediction data and ultrasound biometric and/or physiological or phenomenological pregnancy parameters, as well as the degree of reliability of fetal weight prediction and the consistency with the measurements of ultrasound biometric parameters and/or physiological and/or phenomenological pregnancy parameters of the pregnancy, as a probability value.

FIG. 3 shows the user interface screen of fetal weight estimation, which allows interactive control of measurement errors. The charts of the 5 parameters measured during ultrasound show the mean curves (50th percentile), denoted by C1, and the curves that delimit 95% confidence intervals, denoted by C2 and C3.

The graphic interface for fetal (or neonatal) weight estimation from ultrasound measurements allows interactive control of measurement errors.

The mean and confidence curves are obtained in a fast and efficient manner thanks to the incorporation of two data sets in the software.

A first data set is stored in a file that contains the synaptic weights $\bar{\omega}_m$, the neuron excitation thresholds $\bar{\alpha}_m$ and the structure of the ANNm. A simulated ANNm is used in the software and this allows to trace any mean curve for each input data set consisting of the components of the data vector w, which in this particular preferred embodiment are the amount of Amniotic Fluid (AF), the Number of Fetuses (NF), and the number of Days to Delivery (DD).

A second set contains the covariance matrices for each fetal weight WB. It shall be remembered that, in the model of this invention, the covariance matrices only depend on fetal or neonatal weight WB and are independent of the three other input parameters, which are given in respective windows on the right side of the screen of FIG. 3 and are denoted by numerals 1, 2 and 3. Therefore, the second set consists of a collection of 6000 covariance matrices (5 variances and 10 covariances), each for a different fetal or neonatal weight, in an incremental sequence with one-gram increments and in a range of 1 to 6000 grams. These matrices were obtained from simulated ANNv and ANNC, outside the prediction software whose interface is shown in FIG. 3, and were stored in a data file which may be accessed from the prediction software and allows to trace the curves C2 and C3 as deviations from the corresponding means (curves C1).

In short, the software that represents the multinormal model according to the expression (1) only incorporates the mean curve representing neural network, whereas the covariance matrices are obtained from externally stored data. Thus, the software procedure is highly fast and efficient. It should be noted that the simulated ANNm only requires simple mathematical addition calculations and exponential functions.

The dash line L5 in the window of each ultrasound biometric parameter and at the gestational age MA show the correspondence between the measured value of these parameters ad the fetal weight in grams, corresponding to the mean curve C1 whose value is the most probable weight for the corresponding parameter. The fetal or neonatal weight WB which is estimated as the most probable for each parameter is indicated in a window 6 at the lower end of the corresponding dash line 5, this value being preferably displayed with well visible background-character combinations, such as red character on yellow background. Thus, 5 fetal weight values, corresponding to the mean curves of each component of the measured data vector x are combined together.

The most probable weight for all simultaneously taken parameters (i.e. un a multivariate manner), intended as the value that maximizes the expression (1) among all weight values, has to be found in a narrower range of weights, from the lowest to the highest of these 5 weights.

According to a first embodiment, it is possible to calculate the probabilities associated to all the weights of this range and take the weight that corresponds to the maximum probability. This procedure unfortunately requires very long computation times. The conditioned probability expressed in the equation (1) is identified by the confidence ellipsoid of the parameters which may be in turn calculated by inverting the covariance matrix and calculating the cumulative probability density function Fc for Fischer's distribution F corresponding to the ellipsoid. As is known, matrix inversion involves long computation times.

More specifically, for each fetus k and weight h (h=1, 2, ..., 6000), the associated multivariate probability is:

$$p(x_k / [PN_h\ LA_k\ NF_k\ GP_k]) = 1 - F_c \quad (10)$$

$$\left\{ \frac{1}{d}[x_k - \mu(w)] \sum_{PN}^{T-1} [x_k - \mu(w)], \right.$$

$$\left. d, n \right\}$$

where d=5 is once again the dimensionality of parameter space and n=4000 is the number of cases whereon model estimation was based.

Alternatively to the above, to search for the most probable fetal weight with a substantial reduction of computation times, the invention provides an efficient dichotomous algorithm for determining the maximum or minimum value of a range in which a function only admits one maximum or minimum. The maximum probability is determined by the following steps:

1. Determining the probabilities in the above mentioned range of weights, using the equation (10) at three weight values, i.e. the minimum, maximum and intermediate values respectively;

2. Dividing the range of weights into two half-ranges;

3. Repeating the step 1 in the half-range of weights having the higher pair of extreme probabilities;

4. Further dividing the range into two halves and selecting the new half-range (one quarter of the starting range) like in step 1;

5. 6. . . . : progressively dividing the further ranges into halves;

the steps are repeated until the range is reduced to one point, which coincides with the most probable weight, corresponding to the maximum probability.

Figure 4:
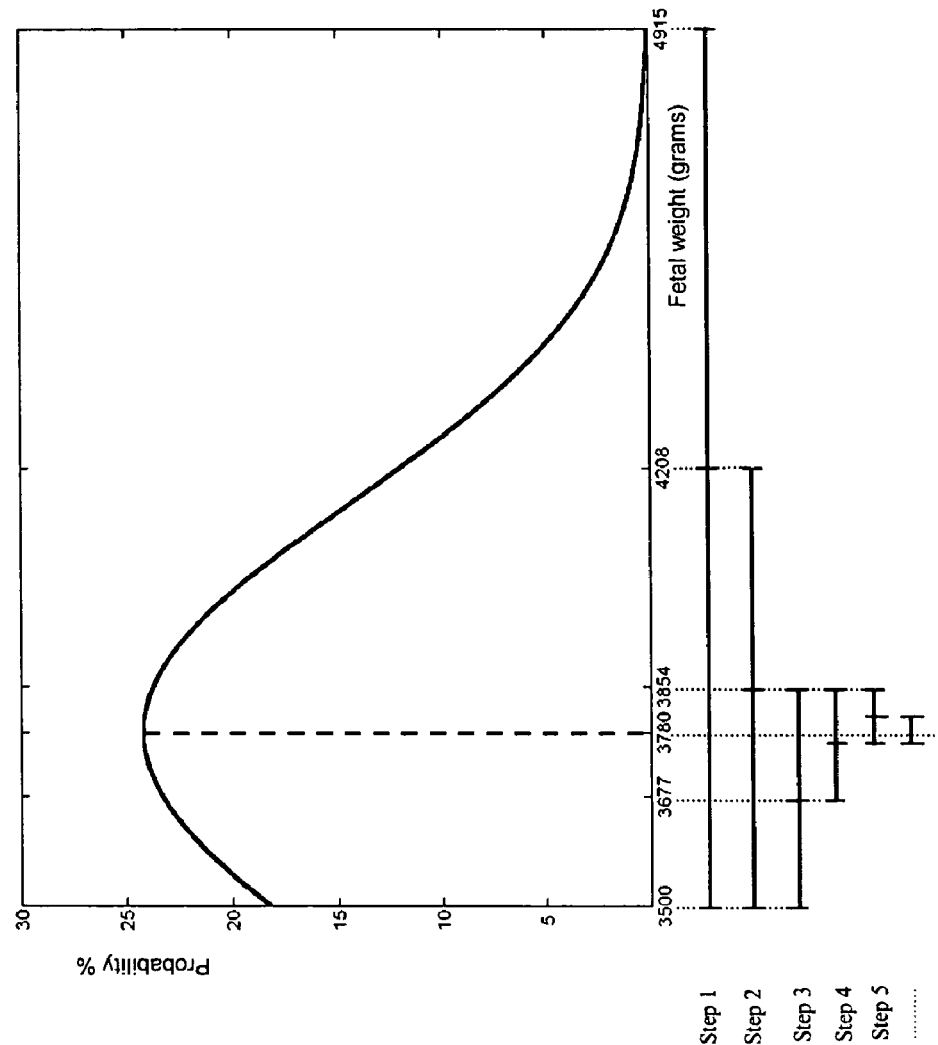
FIG. 4 schematically shows the operation of the dichotomous algorithm for neonatal weight estimation, to find a maximum or a minimum of a function, relating to the case of FIG. 3.

The operation of the dichotomous algorithm for fetal weight estimation, corresponding to the maximum of the multivariate probability is also shown in FIG. 4, which relates to the example of FIG. 3.

The most probable weight value so obtained is assigned a unique probabilistic model, denoted in FIG. 3 by a vertical dash line passing through all the charts for all ultrasound biometric parameters and the gestational age. This line, denoted by numeral 7, defines the most probable estimated weight, which is indicated in window 8, in FIG. 3, and its multivariate probability percent value, which is indicated in an adjacent window 12, but also defines, at the intersection with the mean curves C1, along the horizontal line 13, the most probable values of the ultrasound biometric parameters, which are indicated in window 9 to the right of each chart and their respective deviations from actual measurements, expressed in terms of univariate consistency probability, which are also indicated to the right of each chart, in window 10. Furthermore, the values obtained from parameter measurements are also indicated in the interface screen of FIG. 3, to the right of each chart, in window 11.

An overall weight value having an excessively low multivariate probability can indicate two important alternative or combined possibilities: the baby may be out of normal biological ranges, have wrong measurements, or both. These possibilities are worthy of serious attention. More in detail, the probabilities associated to the individual measured parameters provide real-time data about their consistency with the other measurements. Once more, very low probabilities may indicate that the corresponding parameters may be measured in a wrong manner, or that the fetus has unusual morphological characteristics.

This data, possibly combined with other available data, allow the ultrasound operator to effectively interact with the software and the apparatus, to actually minimize errors and improve estimation accuracy. For instance, if the doctor suspects the measurements to be wrong, he/she may decide to take other measurements or correct their values according to model suggestions, to obtain new estimates and new probabilities, to possibly take new measurements and so on.

These steps, as well as other steps, e.g. to save the estimation session or start prediction, may be controlled by the user by means of one or more virtual buttons which may be accessed and actuated by a mouse or key combinations, such as in the example of FIG. 3, which shows the "Run", "Save" and "Read" buttons 14.

Figure 5:
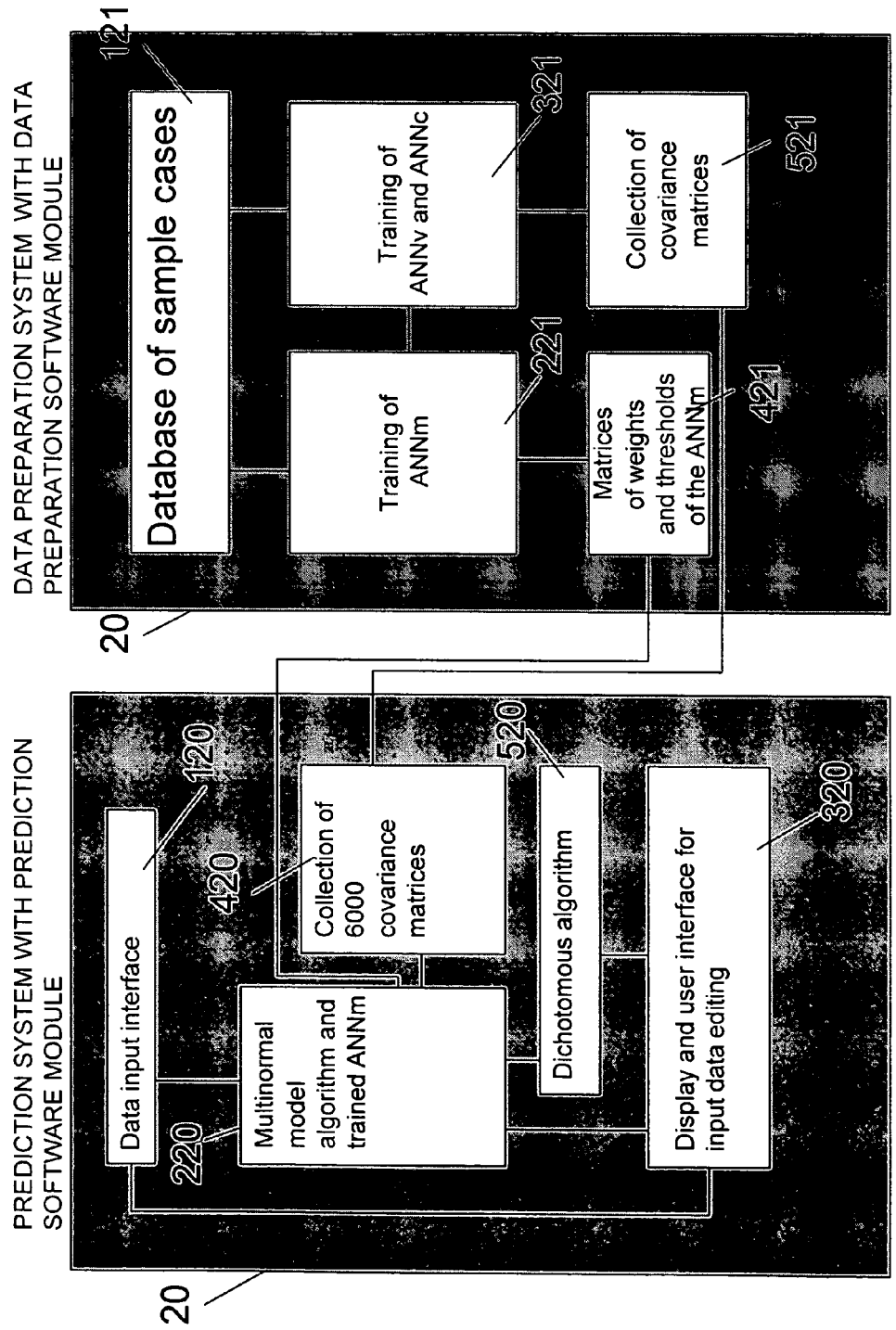
FIG. 5 is a block diagram of one embodiment of the system.

Referring to FIG. 5, the system for carrying out the above method comprises a computer having at least one data input device and at least one display monitor and in which a computer program is or may be loaded, wherein the algorithms of the multinormal model, the interfaces for access to sample case database data, and the algorithms of the mean vector and covariance matrix estimation model, as well as the code for displaying the neonatal weight estimate and the probability thereof are coded.

The program has a neonatal weight prediction module 20, which may be executed in a computer, and an independent preparation module 21, which may be executed in an additional apparatus, the neonatal weight prediction module only having the code for the multinormal model and for the first neural network, trained with the database of sample cases for estimation of the mean values of said ultrasound biometric parameters, and of said one or more physiological and/or phenomenological pregnancy parameters, i.e. the components of the mean vector $\mu(w)$. This obviously means that the trained network is associated to the corresponding matrix of weights and synaptic activation thresholds. Thus, the prediction module has a computation algorithm coded therein, for predicting the most probable neonatal weight, for each ultrasound biometric parameter and/or for one or more physiological and/or phenomenological pregnancy parameters.

A data input interface section 120 is interfaced with a multinormal model computation section 220 for predicting the neonatal and fetal weight from input data, which comprises the code for the multinormal model, as expressed in the function (1), and for the first neural network ANNm, trained with the database of sample cases to estimate the mean values of said ultrasound biometric parameters and said one or more physiological and/or phenomenological pregnancy parameters, i.e. the components of the mean vector μ(w) as well as the matrix of weights and thresholds of said trained network. The output of this section 220 is directly connected to the input of a display and graphic interface section 320, which determines the probability curves in the form of a value for each ultrasound parameter and/or for each of the one or more physiological and phenomenological pregnancy parameters, corresponding to the 50th percentile. The section 420 comprises the tables of covariance matrices which allow to determine the curves that delimit a 95% confidence interval, which curves are traced and displayed by the display and interface section 320.

The display and graphic user interface section traces, in vertically adjacent and aligned positions, the 50th percentile probability curve for each ultrasound biometric parameter and/or each physiological and/or phenomenological pregnancy parameter as a function of the neonatal weight, and the curves that delimit a 95% confidence interval, said curves being traced in different colors and/or different gray tones and/or different graphic aspects, whereas the predicted and most probable neonatal weight for each ultrasound biometric parameter and for each of the one or more physiological and/or phenomenological pregnancy parameters is determined from said 50th percentile probability curve to the value of the corresponding ultrasound biometric parameter and of the corresponding physiological or phenomenological pregnancy parameter, and is graphically indicated by a dash line intersecting the neonatal weight scale at the intersection of said 50th percentile probability curve with the line that passes through the value of the corresponding ultrasound biometric parameter or the corresponding physiological or phenomenological pregnancy parameter. Particularly, this display and interface section comprises the code to execute the functions described with reference to FIG. 3.

Furthermore, the prediction module comprises the section 520, in which a computation algorithm is coded for determining the most probable fetal or neonatal weight, for all ultrasound biometric parameters and/or for one or more of the physiological and/or phenomenological pregnancy parameters. The output of this section 520 is also provided to the display and user interface section 320.

The independent preparation module 21, which may be executed on an independent apparatus, separately from the prediction module 20, comprises a section for input of the database of sample data and a section 221 for preparation of the tables of covariance matrices on the basis of sample data, in which the algorithms of the second and third neural networks are coded for estimating the values of the covariance matrix Σ(w) to generate a database of covariance matrices, each determined for a different neonatal weight of a set of neonatal weights in a predetermined range, particularly from 1 g to 6000 g, in 1 g increments, which database of covariance matrices is provided as a reference database for computing the neonatal weight prediction in combination with the prediction module, and may be accessed by said module for computation of said prediction.

The preparation module 21 also comprises a section 321 for training the first neural network ANNm in which the algorithm of said first neural network is coded for training thereof, and provides at its output the trained network and the corresponding matrix of weights and thresholds.

The table of covariance matrices 521 and the trained neural network ANNm, with the corresponding matrix of weights and synaptic activation thresholds 421 are provided at the output of the preparation module 21 and are integrated in the prediction module 20, which does not have to compute this data every time it is executed. On the contrary, the neural network ANNm and the corresponding matrices of weights and synaptic activation thresholds and/or the table of the covariance matrices are computed once, before execution of the prediction module. The neural network ANNm and its respective matrices of weights and synaptic activation thresholds and/or the table of covariance matrices may be computed once in a while at regular intervals to refine and improve the performances of the networks and data and the prediction module may be submitted at regular intervals to maintenance, consisting in updating the code of the updated neural network ANNm and its respective matrices of weights and synaptic activation thresholds and/or in updating the table of covariance matrices.

According to a variant of the method and system of this invention, considering that some populations have an averagely lower body weight (e.g. Asiatic populations) or possibly a higher body weight, the physiological and/or phenomenological pregnancy parameter, particularly said menstrual age (MA) parameter, is not displayed and cannot be corrected. This does not change the method and system in any manner. The only difference is that the menstrual age is not shown on the screen as a parameter to be edited. The MA is entered once by the ultrasound operator to be possibly corrected internally by the system which brings it back to the most probable value, as provided by the model. This allows to provide a MA value that is constantly consistent with ultrasound biometric measurements, for any ethnic group. Conversely, by allowing manual editing of said menstrual age MA parameter in an inhomogeneous condition of the relevant ethnic group, this parameter might be inconsistent for populations in which, given the same fetal dimensions, a higher or lower MA would be obtained.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. A method for fetal weight estimation, comprising the following steps:
   a) ultrasonically measuring fetal biometric parameters for a plurality of sample cases;
   b) determining physiological and phenomenological pregnancy parameters for each sample case of said plurality of sample cases;
   c) determining a fetal weight for each of the sample cases by precision weighing at birth;
   d) creating a database of the sample cases in which each record associated to each known case comprises the fetal biometric parameters, the physiological and phenomenological pregnancy parameters and the fetal weight as determined at birth;
   e) generating mathematical prediction models from the database of the sample cases;
   f) ultrasonically measuring said fetal biometric parameters of a case under examination for which fetal weight is to be predicted;
   g) determining further physiological and phenomenological pregnancy parameters of the case under examination;
   h) predicting the fetal weight of the case under examination by using the mathematical prediction models generated in step d), wherein a multinormal probabilistic model is used as the mathematical model, said predicting step providing an estimation of a most probable fetal weight, as a multinormal probabilistic model maximizing value over all the fetal weights, wherein said multinormal probabilistic model is governed by the following function which provides a probability density of the measured fetal biometric parameters and one or more of the physiological and phenomenological pregnancy parameters, the probability density is conditioned by information relating to the physiological and phenomenological pregnancy parameters and the fetal weights of the sample cases:

$$p(x/w) = \frac{1}{(2\pi)^{d/2}|\Sigma(w)|^{1/2}} \exp\left\{-\frac{1}{2}[x-\mu(w)]^T \sum_{w}^{-1}[x-\mu(w)]\right\} \quad (1)$$

where:
- x is an observation vector, including the measured ultrasound biometric parameters of the fetus and one or more physiological and phenomenological pregnancy parameters, wherein the observation vector comprises, as components, variables xi, i=1, 2, ... n, each relating to one of measured ultrasound biometric parameters of the fetus and of the one or more physiological and phenomenological pregnancy parameters,
- w is a data vector containing, as components, the variables wj, j=1,2, ... ,k, each being composed of the weight at birth and of one of the other physiological and phenomenological pregnancy parameters,
- d is a dimension of a multidimensional space of the measured ultrasound biometric parameters of the fetus, and one or more physiological and phenomenological pregnancy parameters which form components of the vector x, with d=n,
- $\mu(w)$ and $\Sigma(w)$ are a mean vector and a covariance matrix, respectively, of the mean value xim of the components xi of the data vector x;

i) computing a plurality of probability curves by the multinormal probabilistic model for at least one component of the observation vector x and at least one of the physiological and phenomenological pregnancy parameters that form the components of the data vector w;

j) after determining the plurality of probability curves for at least one of the one or more physiological and phenomenological pregnancy parameters, automatically correcting the parameter during estimation of the most probable fetal weight value for at least some or all of the ultrasound biometric parameters and at least one of the physiological and phenomenological pregnancy parameters;

k) determining a set of most probable values of the ultrasound biometric parameters and at least one of the physiological and phenomenological pregnancy parameters;

l) determining a set of deviations of the most probable values from the measured values of said ultrasound biometric parameters and at least one of the physiological and phenomenological pregnancy parameters, the deviations are expressed in terms of univariate probability of consistency with the most probable fetal weight; and m) displaying the probability curves, the most probable values and the deviations.

2. The method of claim 1, wherein the mean vector $\mu(w)$ and the covariance matrix $\Sigma(w)$ are determined by estimation using the data of the database of sample cases.

3. The method of claim 1, wherein the mean vector $\mu(w)$ and the covariance matrix $\Sigma(w)$ are determined by mathematical computation using the data of the database of sample cases.

4. The method of claim 1, wherein the mean vector $\mu(w)$ is computed from the data of the database of sample cases using the following expression:

$$\overline{\mu}_i(w) = \frac{\sum_{k=1}^{N} x_{i_k}(w)}{N}$$

where summations are extended to all N data of each component xi, which have a combination of values that is the same as the data vector w, said computing step being repeated for combination of w.

5. The method of claim 4, wherein the elements of the covariance matrix $\Sigma(w)$ defined as $$\Sigma(w) = \begin{bmatrix} \sigma_{x_1}^2(w) & \sigma_{x_1 x_2}(w) & \sigma_{x_1 x_3}(w) & \sigma_{x_1 x_4}(w) & \sigma_{x_1 x_5}(w) \\ \sigma_{x_2 x_1}(w) & \sigma_{x_2}^2(w) & \sigma_{x_2 x_3}(w) & \sigma_{x_2 x_4}(w) & \sigma_{x_2 x_5}(w) \\ \sigma_{x_3 x_1}(w) & \sigma_{x_3 x_2}(w) & \sigma_{x_3}^2(w) & \sigma_{x_3 x_4}(w) & \sigma_{x_3 x_5}(w) \\ \sigma_{x_4 x_1}(w) & \sigma_{x_4 x_2}(w) & \sigma_{x_4 x_3}(w) & \sigma_{x_4}^2(w) & \sigma_{x_4 x_5}(w) \\ \sigma_{x_5 x_1}(w) & \sigma_{x_5 x_2}(w) & \sigma_{x_5 x_3}(w) & \sigma_{x_5 x_4}(w) & \sigma_{x_5}^2(w) \end{bmatrix}$$

are determined by the following functions $$\overline{\sigma}_{x_i}^2(w) = \frac{\sum_{k=1}^{N} [x_{i_k}(w) - \overline{\mu}_i(w)]^2}{N-1}$$

and $$\overline{\sigma}_{x_i x_j}(w) = \frac{\sum_{k=1}^{N} [x_{i_k}(w) - \overline{\mu}_i(w)][x_{j_k}(w) - \overline{\mu}_j(w)]}{N-1}$$

where summations are extended to all N data of each component xi, which have the same combination of values as the data vector w, said determining step being repeated for combination of w.

6. The method of claim 5 further comprising the step of reducing the number of combinations of the values for the components of the data vector w.

7. The method of claim 5 further comprising the step of imposing a mathematical rule of dependency from the values of the components of the data vector w on the parameters to be estimated, said mathematical rule of dependency is parametrized by estimating the parameters of such functions with appropriate regression methods.

8. The method of claim 1, wherein the mean vector $\mu(w)$ and the covariance matrix $\Sigma(w)$ are determined using non linear predictive algorithms that are trained with the data of the database of sample cases.

9. The method of claim 8, wherein the predictive algorithms are artificial neural networks.

10. The method of claim 9, wherein three artificial neural networks are used: a first artificial neural network (ANNm) for estimating the mean vector μ(w), a second artificial neural network (ANNv) for estimating the variances (diagonal elements) of the covariance matrix Σ(w) and a third artificial neural network (ANNc) for estimating the covariances of said covariance matrix Σ(w).

11. The method of claim 10 further comprising the steps:
training the first artificial neural network (ANNm) with the data of the database of sample cases, to estimate the components of the mean vector μ(w), by presenting thereto the components of the data vector w as input data and the components of the observation vector x as output data, and determining synaptic weights ω(w,x) and activation thresholds α(w,x) depending on the components of the observation vector x, the first artificial neural network (ANNm) having an input;
on the basis of such synaptic weights $\overline{\omega}_m$ and neuron activating thresholds $\overline{\alpha}_m$, using the first artificial neural network (ANNm) for estimating the components of the mean vector μ(w) to determine the estimates of the mean values of the components of the observation vector x by presenting to the input of said first artificial neural network (ANNm), the values of the components of the data vector w;
determining deviations between each component of the observation vector x and the mean value of the corresponding component of the observation vector x as determined by the first neural network, that was trained in the previous steps;
squaring said deviations and placing them at an output of the second artificial neural network (ANNv) for variance estimation, which is trained by presenting to its input the components of the corresponding data vector w; and
multiplying said deviations together and placing them at an output of the third artificial neural network (ANNc) for covariance estimation, which is trained by presenting to its input the components of the corresponding data vector w,
wherein said neural networks are used to estimate the components of the mean vector μ(w) and the covariance matrix Σ(w) of the multinormal probabilistic model from the ultrasound biometric parameters and one or more measured physiological and/or phenomenological pregnancy parameters, which form the components of the observation vector x, and the other measured physiological and/or phenomenological pregnancy parameters, which form the components of the data vector w to be added to the fetal weight value, and
said multinormal probabilistic model is used to compute the probability curves for each or a subgroup of the components of the observation vector x, which represent the relation between each of the components of the observation vector x.

12. The method of claim 11 further comprising the step of presenting only the fetal weight component of the data vector w during training of the second artificial neural network (ANNv) for variance estimation, and the third artificial neural network (ANNc) for covariance estimation.

13. The method of claim 11, further comprising the step of estimating the covariance matrices using the second and third artificial neural networks after training thereof, and the covariance matrices are obtained as a function of different fetal weights imposed on said neural networks in a range of 0 to 6000 grams.

14. The method of claim 11, further comprising the steps of computing and storing the covariance matrices computed using the second and third artificial neural networks after training thereof, and the covariance matrices are obtained for each weight at birth determined in progressive 1 gram increments with respect to the previously imposed weight and in a range of 0 to 6000 grams, for use in the computation of the multinormal probabilistic model and the probability curves that delimit the confidence intervals.

15. The method of claim 1, further comprising the step of determining a 50th percentile mean probability curve and a plurality of probability curves that delimit a 95% confidence interval for each of the components of the observation vector x.

16. The method of claim 15, further comprising the step of, for each of the components of the observation vector x, determining a fetal weight as a value of the mean probability curve corresponding to said measured ultrasound biometric parameter or physiological and/or phenomenological pregnancy parameter, said fetal weight provides a most probable fetal weight value for the corresponding measured ultrasound biometric parameter or physiological and phenomenological pregnancy parameter.

17. The method of claim 1, wherein the most probable fetal weight value is determined as a multinormal probabilistic model maximizing value over all the weights in a predetermined limited range of fetal weight values.

18. The method of claim 17, wherein said limited range of fetal weight values is delimited by a minimum and a maximum fetal weight values among the fetal weights that have been determined as the most probable values for each ultrasound biometric parameter and each of the one or more physiological and/or phenomenological pregnancy parameters that have been measured.

19. The method of claim 1, wherein a dichotomous algorithm is used to find a minimum or a maximum value in a range of predetermined fetal weight values.

20. The method of claim 19, wherein the dichotomous algorithm provides the following steps:
determining the probabilities in the predetermined range of fetal weight values, at three weight values, the minimum, maximum and intermediate values respectively, using the function $$p(x_k / [w_k]) = 1 - F_c$$
$$\left\{ \frac{1}{d} [x_k - \mu(w)]^T \sum_{PN}^{-1} [x_k - \mu(w)], d, n \right\}$$

where:
d is a dimensionality of the space of the components of the observation vector x, the number of ultrasound biometric parameters and of the one or more physiological and phenomenological pregnancy parameters,
n is the number of sample cases in the database whereon the multinormal probabilistic model estimation was based,
k is the ordinal number of each fetus, and
h is the fetal weight value for fetus k;
dividing the range of weights into two half-ranges;
repeating the first step in the half-range of weights having the higher pair of extreme probabilities;

further dividing the range into two halves and selecting the new half-range (one quarter of the starting range) like in the first step;

progressively dividing the further ranges into halves; and in further steps stopping the halving steps when the range is reduced to one point, which coincides with the most probable weight, corresponding to the maximum probability.

21. The method of claim 1, wherein the fetal biometric parameters are the following quantities:

head circumference (HC) and abdominal circumference (AC), biparietal diameter (BPD) and femur length (FL), as measured in ultrasound images of the fetus in the final pregnancy stage.

22. The method of claim 1, wherein the physiological and phenomenological pregnancy parameters are the following quantities:

the gestational age, which is related to the first day of the last menstrual period (MA) and is determined by an accurate reconstruction of menstrual history, confirmed by an ultrasonographic examination dating before the 20th week of gestation, the amount of amniotic fluid (AF) and the number of days to delivery (DD).

23. A system for estimating fetal weight, said system comprising a computer, an input device communicatively connected to the computer, a display monitor, and a computer program is loaded onto the computer, the computer program is constructed and arranged to perform the method of claim 1, wherein a plurality of algorithms of the multinounal probabilistic model, a plurality of interfaces for access to the sample case database, a plurality of algorithms of the mean vector and covariance matrix model, and code for displaying the predicted fetal weight and a probability thereof are coded on the program.

24. The system of claim 23, wherein the program has a neonatal weight prediction module which is executable by the computer, and an independent preparation module, which is executable by an additional apparatus, the neonatal weight prediction module having a first neural network trained with the database of sample cases for estimation of a set of mean values of said ultrasound biometric parameters and of said one or more physiological and/or phenomenological pregnancy parameters, whereas the independent preparation module comprises the algorithms of a second and third neural networks for estimation of the values of a covariance matrix $\Sigma(w)$ to generate a database of covariance matrices, each determined for a different neonatal weight of a set of neonatal weights in a predetermined range, particularly from 0 g to 6000 g, in 1 g increments, which database of covariance matrices is provided as a reference database for computing the neonatal weight prediction in combination with the prediction module, and is accessed by said module for computation of said prediction.

25. The system of claim 24, wherein the prediction module has a computation algorithm coded therein, for predicting the most probable neonatal weight, for each ultrasound biometric parameter and/or for one or more physiological and/or phenomenological pregnancy parameters.

26. The system of claim 25, wherein the prediction module comprises an algorithm for determining a plurality of 50th percentile probability curves in the form of the value of some or each of the ultrasound biometric parameters and/or for some or each of the one or more physiological and/or phenomenological pregnancy parameters, as well as the curves that delimit a 95% confidence interval.

27. The system of claim 26, wherein the neonatal weight prediction module comprises a display and graphic user interface program, which traces, in vertically adjacent and aligned positions, the 50th percentile probability curve for some or each of the ultrasound biometric parameters and/or some or each of the physiological and/or phenomenological pregnancy parameters as a function of the neonatal weight, and the curves that delimit the 95% confidence interval, said curves being traced in different colors and/or different gray tones and/or different graphic aspects, whereas the predicted and most probable neonatal weight for each ultrasound biometric parameter and for each of the one or more physiological and/or phenomenological pregnancy parameters is determined from said 50th percentile probability curve to the value of the corresponding ultrasound biometric parameter and of the corresponding physiological or phenomenological pregnancy parameter, and is graphically indicated by a dash line intersecting the neonatal weight scale at the intersection of said 50th percentile probability curve with the line that passes through the value of the corresponding ultrasound biometric parameter or the corresponding physiological or phenomenological pregnancy parameter.

28. The system of claim 27, wherein the value of the ultrasound biometric parameter or the corresponding physiological or phenomenological pregnancy parameter and the corresponding predicted neonatal weight are displayed in numeric form.

29. The system of claim 28, wherein the prediction module comprises a dichotomous algorithm for determining the most probable neonatal weight estimation value, for some or all of the ultrasound biometric parameters and/or for some or all of the one or more physiological and/or phenomenological pregnancy parameters, taken simultaneously, and graphic and alphanumeric representation thereof, as well as of the probability of said neonatal weight prediction by displaying a line passing through some or all of the 50th percentile probability curve charts for the individual ultrasound biometric parameters and the one or more physiological and/or phenomenological pregnancy parameters, which the algorithm determines, from an intersection of said line indicating the most probable fetal weight for some or all of the ultrasound biometric parameters and some or all of the one or more physiological or phenomenological pregnancy parameters, taken simultaneously, with the corresponding 50th percentile probability curve, the value of each of said ultrasound biometric parameters and each of said one or more physiological of phenomenological pregnancy parameters, corresponding to said most probable neonatal weight for all the ultrasound biometric parameters and for all of the one or more physiological or phenomenological pregnancy parameters, taken simultaneously, as well as a deviation thereof from the measured values in the form of measurement correctness probability, said values being also displayed in alphanumeric form.

30. The system of claim 29, wherein the prediction module comprises a control interface for editing the measured values of one or more or all of the ultrasound biometric parameters and one or more of the physiological or phenomenological pregnancy parameters.

31. A method for fetal weight estimation, comprising the following steps:

a) ultrasonically measuring fetal biometric parameters for a plurality of sample cases;

b) determining physiological and phenomenological pregnancy parameters for each sample case of said plurality of sample cases;

c) determining a fetal weight for each of the sample cases by precision weighing at birth;

d) creating a database of the sample cases in which each record associated to each known case comprises the fetal biometric parameters, the physiological and phenomenological pregnancy parameters and the fetal weight as determined at birth;

e) generating mathematical prediction models from the database of the sample cases;

f) ultrasonically measuring said fetal biometric parameters of a case under examination for which fetal weight is to be predicted;

g) determining further physiological and phenomenological pregnancy parameters of the case under examination;

h) predicting the fetal weight of the case under examination by using the mathematical prediction models generated in step e), wherein a multinormal probabilistic model is used as the mathematical model, said predicting step providing an estimation of a most probable fetal weight, as a multinormal probabilistic model maximizing value over all the fetal weights, wherein said multinormal probabilistic model is governed by the following function which provides a probability density of the measured fetal biometric parameters and one or more of the physiological and phenomenological pregnancy parameters, the probability density is conditioned by information relating to the physiological and phenomenological pregnancy parameters and the fetal weights of the sample cases:

$$p(x/w) = \frac{1}{(2\pi)^{d/2}|\Sigma(w)|^{1/2}} \exp\left\{-\frac{1}{2}[x - \mu(w)]^T \Sigma_w^{-1} [x - \mu(w)]\right\}$$

where:
- x is an observation vector, including the measured ultrasound biometric parameters of the fetus and one or more physiological and phenomenological pregnancy parameters, wherein the observation vector comprises, as components, variables $x_i$, $i=1, 2, \ldots n$, each relating to one of the measured ultrasound biometric parameters of the fetus and of the one or more physiological and phenomenological pregnancy parameters,
- w is a data vector containing, as components, the variables $w_j$, $j=1,2,\ldots,k$, each being composed of the weight at birth and of one of the other physiological and phenomenological pregnancy parameters,
- d is a dimension of a multidimensional space of the measured ultrasound biometric parameters of the fetus, and one or more physiological and phenomenological pregnancy parameters which form components of the vector x, with $d=n$,
- $\mu(w)$ and $\Sigma(w)$ are a mean vector and a covariance matrix, respectively, of the mean value $x_{im}$ of the components $x_i$ of the data vector x, as functions of said data vector w, the mean vector $\mu(w)$ and the covariance matrix $\Sigma(w)$ are determined using non linear predictive algorithms that are trained with the data of the database of sample cases, the predictive algorithms are three artificial neural networks comprising a first artificial neural network (ANNm) for estimating the mean vector $\mu(w)$, a second artificial neural network (ANNv) for estimating the variances (diagonal elements) of the covariance matrix $\Sigma(w)$ and a third artificial neural network (ANNc) for estimating the covariances of the same covariance matrix $\Sigma(w)$;

i) training the first artificial neural network (ANNm) with the data of the database of sample cases, to estimate the components of the mean vector $\mu(w)$, by presenting thereto the components of the data vector w as input data and the components of the observation vector x as output data, and determining synaptic weights $\omega(w,x)$ and activation thresholds $\alpha(w,x)$ depending on the components of the observation vector x, the first artificial neural network (ANNm) having an input;

j) on the basis of such synaptic weights $\bar{\omega}_m$, and neuron activating thresholds $\bar{\alpha}_m$, using the first artificial neural network (ANNm) for estimating the components of the mean vector $\mu(w)$ to determine the estimates of the mean values of the components of the observation vector x by presenting to the input of said first artificial neural network (ANNm), the values of the components of the data vector w;

k) determining deviations between each component of the observation vector x and the mean value of the corresponding component of the observation vector x as determined by the first neural network, that was trained in the previous steps;

l) squaring said deviations and placing them at an output of the second artificial neural network (ANNv) for variance estimation, which is trained by presenting to its input the components of the corresponding data vector w;

m) multiplying said deviations together and placing them at an output of the third artificial neural network (ANNc) for covariance estimation, which is trained by presenting to its input the components of the corresponding data vector w, wherein said neural networks are used to estimate the components of the mean vector $\mu(w)$ and the covariance matrix $\Sigma(w)$ of the multinormal probabilistic model from the ultrasound biometric parameters and one or more measured physiological and/or phenomenological pregnancy parameters, which form the components of the observation vector x, and the other measured physiological and/or phenomenological pregnancy parameters, which form the components of the data vector w to be added to the fetal weight value;

n) computing a plurality of probability curves by the multinormal probabilistic model for at least one component of the observation vector x and at least one of the physiological and phenomenological pregnancy parameters that form the components of the data vector w;

o) determining a set of most probable values of the ultrasound biometric parameters and at least one of the physiological and phenomenological pregnancy parameters;

p) determining a set of deviations of the most probable values from the measured values of said ultrasound biometric parameters and at least one of the physiological and phenomenological pregnancy parameters, the deviations are expressed in terms of univariate probability of consistency with the most probable fetal weight; and q) displaying the probability curves, the most probable values and the deviations.

* * * * *

UNITED STATES PATENT AND TRADEMARK OFFICE
CERTIFICATE OF CORRECTION

| | | |
|---|---|---|
| PATENT NO. | : 8,012,091 B2 | Page 1 of 1 |
| APPLICATION NO. | : 11/484099 | |
| DATED | : September 6, 2011 | |
| INVENTOR(S) | : Petraglia et al. | |

It is certified that error appears in the above-identified patent and that said Letters Patent is hereby corrected as shown below:

In column 15, line 42, following the words "vector x" and before the ";", please add --as functions of said data vector w--.

Signed and Sealed this
Sixth Day of December, 2011

David J. Kappos
*Director of the United States Patent and Trademark Office*